(12) United States Patent
Ji et al.

(10) Patent No.: US 7,319,174 B2
(45) Date of Patent: Jan. 15, 2008

(54) DRY-ETCHING GAS FOR SEMICONDUCTOR PROCESS AND PREPARATION METHOD THEREOF

(75) Inventors: Hae Seok Ji, Disan (KR); Ook Jae Cho, Ulsan (KR); Jae Gug Ryu, Disan (KR); Jong Yeol Yang, Disan (KR); Young Hoon Ahn, Ulsan (KR); Bong Suk Kim, Disan (KR); Dong Hyun Kim, Disan (KR)

(73) Assignee: Ulsan Chemical Co., Ltd., Nam-ku, Ulsan (KR)

( * ) Notice: Subject to any disclaimer, the term of this patent is extended or adjusted under 35 U.S.C. 154(b) by 0 days.

(21) Appl. No.: 11/535,035

(22) Filed: Sep. 25, 2006

(65) Prior Publication Data

US 2007/0265478 A1    Nov. 15, 2007

(30) Foreign Application Priority Data

May 9, 2006    (KR) ..................... 10-2006-0041370

(51) Int. Cl.
*C07C 17/20* (2006.01)
*C09K 13/00* (2006.01)
(52) U.S. Cl. ..................................... 570/160; 252/79.1
(58) Field of Classification Search ................ 570/160; 252/79.1
See application file for complete search history.

(56) References Cited

U.S. PATENT DOCUMENTS 6,395,940 B1 *  5/2002  Komata et al. ............. 570/160
6,884,365 B1 *  4/2005  Hirayama et al. ......... 252/79.1

\* cited by examiner

*Primary Examiner*—J. Parsa
(74) *Attorney, Agent, or Firm*—Egbert Law Office

(57) ABSTRACT

The invention is a method for continuously preparing highly pure octafluorocyclopentene for use in dry-etching processes. The method includes reacting octachlorocyclopentene with KF in a continuous manner, and purifying crude octafluorocyclopentene. In the reacting step, two KF-charged filters are installed in parallel and allowed to communicate with a reactor containing octachlorocyclopentene in an alternating manner to produce crude octafluorocyclopentene. In the purifying step, organics having lower boiling points than octafluorocyclopentene are removed, and metal ingredients and organics having boiling points higher than octafluorocyclopentene are separated to recover octafluorocyclopentene as a gas. The gaseous octafluorocyclopentene composition contains $C_5F_8$ in an amount of 99.995 vol % or higher, nitrogen in an amount of 50 vol ppm or less, oxygen in an amount of 5 vol ppm or less, water in an amount of 5 vol ppm or less, and metal ingredients in an amount of 5 wt ppb or less.

6 Claims, 3 Drawing Sheets

DRY-ETCHING GAS FOR SEMICONDUCTOR PROCESS AND PREPARATION METHOD THEREOF

CROSS-REFERENCE TO RELATED U.S. APPLICATIONS

Not applicable.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

BACKGROUND OF THE INVENTION

1. Field of the Invention

The present invention relates to highly pure octafluorocyclopentene, useful as a dry-etching gas for use in forming a very large scale integrated circuit (hereinafter referred to as "VLSI") pattern or an ultra large scale integrated circuit (hereinafter referred to as "ULSI") pattern, and a preparation method thereof. More particularly, the present invention relates to a dry etching gas containing octafluorocyclopentene ($C_5F_8$) in an amount of 99.995 vol % or greater, nitrogen gas in an amount of 50 vol ppm or less, oxygen gas in an amount of 5 vol ppm or less, water in an amount of 5 wt ppm or less, and metal ingredients in a total amount of 5 wt ppb or less, and a method for preparing the dry-etching gas in a continuous manner with octachlorocyclopentene serving as a starting material.

2. Description of Related Art Including Information Disclosed Under 37 CFR 1.97 and 37 CFR 1.98.

Dry etching, which refers to the removal of material, typically a masked pattern of semiconductor material, is regarded as an essential process for the fabrication of ULSI, which requires ultra-fine patterns of circuits for storage of a great quantity of information within a small space. When a dry etching process is applied to a layer of silicon oxide, which is typical of silicon compounds, conventional etching gas, that is, saturated fluorocarbon gas, cannot ensure patterning circuits to a fineness of 0.13 µm or less (an aspect ratio of 20 or greater). Saturated fluorocarbons exhibit low selectivity between a silicon oxide compound to be etched and a protecting film, e.g., photoresist or polysilicon, so that they are difficult to apply for etching ultra-fine patterns. After etching, in addition, carbon residues of the conventional etching gas are not completely removed, impeding the formation of ultra-fine patterns.

As an alternative etching gas to conventional saturated fluorocarbons, octafluorocyclopentene (hereinafter referred to as "$C_5F_8$"), which contains one double bond, has attracted intensive attention. Thanks to fewer fluorine atoms per carbon atom resulting from the double bond, this alternative etching gas can more selectively etch mask films, such as photoresists, polysilicon, etc., than saturated fluorocarbons. In addition, post-etching residues of the etching gas are readily evaporated, which is helpful for the formation of circuit patterns having a fineness of 0.13 µm or smaller (an aspect ratio of 20 or higher).

$C_5F_8$ is a matrix material having a boiling point of 26.8° C.

With the tendency of semiconductor devices toward high integration and performance, etching gas, such as $C_5F_8$, for use in the formation of semiconductor elements, is required to be purer. High purity is a condition essential in order for etching gas to conduct etching at a high rate and uniformly. The biggest problem in achieving a highly pure etching gas is residual trace components, which are typically metal. A level of metal ingredients higher than a critical level is not only fatal to the formation of fine patterns, but also has a negative influence on the performance of the semiconductor device. Accordingly, etching gas is most strictly controlled during the fabrication procedure of semiconductor devices as well as during the production and purification thereof. It has recently been required to reduce the level of metal ingredients to less than 5 ppb.

Methods of producing highly pure $C_5F_8$ have already been suggested.

Japanese Patent Laid-Open Publication No. Hei. 9-95418 discloses a method of preparing $C_5F_8$ at 99.8-99.98% purity by reacting 1,2-dichlorohexafluorocyclopentene with KF in DMF under a stream of nitrogen.

In International Patent Publication No. WO 2000/71497 (PCT/JP2000/03308) is disclosed a gas for plasma reaction, characterized in that the gas has a content of octafluorocyclopentene of 99.9 vol % or more, and the total amount of nitrogen and oxygen contained as residual trace gas components is 200 vol ppm or less. It can be produced by rectifying crude $C_5F_8$ from a purity of 95 vol % to a purity of 99.9 vol % or more in an atmosphere of an inert gas belonging to Group 0, and subsequently removing residual impurities therefrom through low-temperature vacuum deareation, molecular screening, or absorbent contact.

In typical method of producing $C_5F_8$, octachlorocyclopentene ($C_5Cl_8$) or hexachlorocyclopentadiene ($C_5Cl_6$) is hydrofluorinated with hydrogen fluoride (HF) in the presence of an antimony (Sb) or chrome (Cr) catalyst to partially substitute the chlorine atoms with fluorine atoms to afford chlorofluorocyclopentenes ($C_5Cl_xF_{8-x}$, x=1-7) (U.S. Pat. No. 6,395,940), followed by further fluorinating the chlorofluorocyclopentenes with potassium fluoride (KF) in N,N-dimethylformamide (hereinafter referred to as "DMF") to substitute the chlorine atoms linked to the double bonds with fluorine atoms (Japanese Pat. Laid-Open Publication No. 9-95458).

Chlorine atoms linked to double-bonded carbon atoms are hard to substitute with fluorine atoms using hydrogen fluoride in the presence of an antimony or chromic catalyst. The fluorination of chlorine atoms linked to double-bonded carbon atoms is, accordingly, achieved using potassium fluoride, which requires an additional process step. For fluorination with hydrogen fluoride in the presence of an antimony or chrome catalyst, the preparation, activation and regeneration of the catalyst is needed. In addition, the fluorination is accompanied by complicated processes, including the recovery of excess hydrogen fluoride added, treatment of excess hydrogen chloride produced, the absorption of hydrogen chloride in water and in the course of separation between the product and the hydrogen chloride, and the dehydration of the product.

The direct fluorination of octachlorocyclopentene with potassium fluoride has previously been known (J. Org. Chem. 28 112 (1962)). However, most commercial processes do not take the direct fluorination method using potassium fluoride, but are conducted by partially fluorinating octachlorocyclopentene to chlorofluorocyclopentene in the presence of an antimony or chrome catalyst and subsequently converting chlorofluorocyclopentene to octafluorocyclopentene. The reason for avoiding the direct fluorination of octachlorocyclopentene with potassium fluoride is that it is difficult to maintain a continuous process.

The chemical industry, a kind of process industry, is economically favorable in terms of quality control, manpower, and production cost when the processes thereof are conducted in a continuous manner.

1) Difficulty of Conducting Continuous Process

The direct fluorination of octachlorocyclopentene requires a large quantity of solid potassium fluoride (as much as 8 equivalents or more), compared to the required amount for fluorination of partially fluorinated chlorofluorocyclopentene ($CCl_xF_{8-x}$, x=1-3). After the reaction is terminated upon the completion of addition of octachlorocyclopentene, a large quantity of the by-product solid potassium chloride (KCl) is drained, from the reactor, together with the solvent DMF, followed by feeding fresh DMF and potassium fluoride into the reactor and raising the temperature in order to prepare a new round of the reaction. Accordingly, the processes must be conducted in a non-continuous manner in order to remove the large quantity of solid KCl that accumulates in the reactor.

2) Treatment of Potassium Fluoride and Potassium Chloride

When chlorofluorocyclopentene ($CCl_xF_{8-x}$, x=1-3) is fluorinated with potassium fluoride in DMF, the amount of potassium fluoride is reduced to $\frac{1}{8}$ to $\frac{3}{8}$ of the amount required for the fluorination of octachlorocyclopentene. Accordingly, it is relatively easy to treat solid potassium fluoride and potassium chloride. In contrast, the fluorination of octachlorocyclopentene results in the deposition of a large amount of potassium chloride in DMF, thus making it very difficult to treat the potassium fluoride and potassium chloride. Although conducted with the aid of a stirrer, the treatment of the solid (KCl) is not easily solved. Thus, the direct fluorination of octachlorocyclopentene is difficult to apply in practice.

3) Separation of Potassium Chloride from DMF

After the reaction, potassium chloride and DMF are drained from the lower portion of the reactor and separated using a filter so as that the DMF can be reused. The amount of potassium chloride produced is too large to be filtered completely, and it is cumbersome to return the eluted DMF back into the reactor.

International Patent Publication No. WO 2000/71497 discloses a process of preparing $C_5F_8$ to a purity of 99.97 vol % by placing 99.83% pure $C_5F_8$, along with a boiling chip, in a glass flask equipped with a rectification column, purging the rectification column with He gas, and fluxing the reactants within the flask (Example 1), and a process of further rectifying the $C_5F_8$ to a purity of 99.98% in a helium atmosphere (Example 2).

Generally, crude $C_5F_8$, which needs to be purified to be used in the semiconductor field, contains organic components including starting materials, intermediates, and by-products, in addition to water, nitrogen, oxygen and metal ingredients as impurities. It is very difficult to remove the organic components from the crude $C_5F_8$ since organics having boiling points lower and higher than that of $C_5F_8$ coexisting in the organic components.

According to the method of WO 2000/71497, organic materials having boiling points lower than that of $C_5F_8$ are removed using an inert gas belonging to Group 0 to give $C_5F_8$ with a purity of 99.9 vol % or higher while organics higher in boiling point than $C_5F_8$ are filtered using molecular screening or absorbed to an absorbent to yield $C_5F_8$ with a purity of 99.9 vol % or higher.

Nowhere in the method of the patent are the contents of metal components mentioned because the crude $C_5F_8$ used already has a purity of as high as 95 vol % and the purification process is conducted using glass instruments.

In order to apply the method for the production of $C_5F_8$ on an industrial scale, however, on-line analysis is required in real time. In practice, on-line analysis in real time requires the use of metallic reactors and pipes, such as those made from stainless steel, considering the joints between pipes and reaction conditions such as pressure and heat. Accordingly, the products inevitably contain various metal components because they are introduced from the metallic apparatus.

Therefore, the purification method using glass apparatus alone cannot be industrially applied in practice.

Gas for use in fabricating semiconductor devices must be ultra pure. Trace analysis is important in examining the purity of gas. Particularly, $C_5F_8$ gas, which exists as a liquid at room temperature, readily incorporates nitrogen and/or oxygen thereinto from the air. In order to maintain the reliability and accuracy of semiconductor products by not overlooking the incorporation of impurities from the air, the on-line analysis of such etching gas must be conducted in real time in a purification stage or an application stage. Since, according to the $C_5F_8$ purification method of the international patent (supra), which features the use of glass apparatus and an inert gas belonging to Group 0, the distillation, intake, storage and analysis must be conducted in an incomplete airtight condition, the incorporation of nitrogen and/or oxygen into the product $C_5F_8$ is inevitable. In addition, since purified $C_5F_8$ is stored, along with the inert gas of Group 0, in a pressure-resistant container, the inert gas occupies the upper portion of the container. It is therefore difficult to discharge only $C_5F_8$ at a fixed rate in an early stage of semiconductor process or analysis. Indeed, a large volume of $C_5F_8$ gas is discarded prior to semiconductor processes or analysis. Products purified using a gas of Group 0 (He) are very inconvenient for users to treat because the gas discharge is a prerequisite for accurate analysis or reliable semiconductor processes.

BRIEF SUMMARY OF THE INVENTION

It is an object of the present invention to provide an etching gas for use in VLSI or ULSI processes, comprising 99.995 vol % or more of $C_5F_8$, 50 vol % or less of nitrogen gas, 5 vol % or less of oxygen gas, 5 wt ppm or less of water, and 5 wt ppb or less of metal components.

It is another object of the present invention to provide a method for preparing etching gas from the octachlorocyclopentene in a continuous manner on an industrial scale, which features the reduction of metal ingredients, such as Al, Ca, Cu, Fe, Mg, Mn, Na, Ni, Zn, etc., fatal to the formation of ultrafine patterns and the performance of semiconductor devices, to lower than 5 wt ppb, and which removes oxygen, nitrogen and water.

In accordance with the method of the present invention, highly pure octachlorocyclopentene can be produced in a continuous manner, starting with octachlorocyclopentene.

None of the etching gases commercialized or produced thus far contain $C_5F_8$ at a purity of 99.995 vol % with a content of 5 wt ppb or less of metal ingredients.

In order to accomplish the above objects, one aspect of the present invention provides a method for continuously preparing 99.995 vol % or higher pure octafluorocyclopentene, useful as dry etching gas, comprising: (1) reacting octachlorocyclopentene with KF in a continuous manner using a reaction system in which two KF-charged filters are installed in parallel and are allowed to communicate with a reactor containing octachlorocyclopentene in an alternating manner by opening valves between the filters and the reactor in turn, to produce crude octafluorocyclopentene having a purity of 50~80 vol %; and (2) purifying the crude octafluorocyclopentene by removing organics having boiling points lower than that of octafluorocyclopentene from the crude octafluorocyclopentene through fractional distillation and by separating metal ingredients and organics having boiling points higher than that of octafluorocyclopentene through fractional distillation to recover octafluorocyclopentene as a gas, whereby a gaseous octafluorocyclopentene composition containing $C_5F_8$ in an amount of 99.995 vol % or higher, nitrogen in an amount of 50 vol ppm or less, oxygen in an amount of 5 vol ppm or less, water in an amount of 5 vol ppm or less, and metal ingredients in an amount of 5 wt ppb or less can be obtained. The highly pure $C_5F_8$ is very useful as a dry etching gas for use in VLSI or ULSI processes.

In accordance with the method of the present invention, highly pure $C_5F_8$ for use in semiconductor processes can be produced from $C_5Cl_8$ in a continuous manner without the use of gas of Group 0, molecular screens, absorbents, etc.

BRIEF DESCRIPTION OF THE SEVERAL VIEWS OF THE DRAWINGS

The above and other objects, features and advantages of the present invention will be more clearly understood from the following detailed description taken in conjunction with the accompanying drawings.

DETAILED DESCRIPTION OF THE INVENTION

Figure 1:
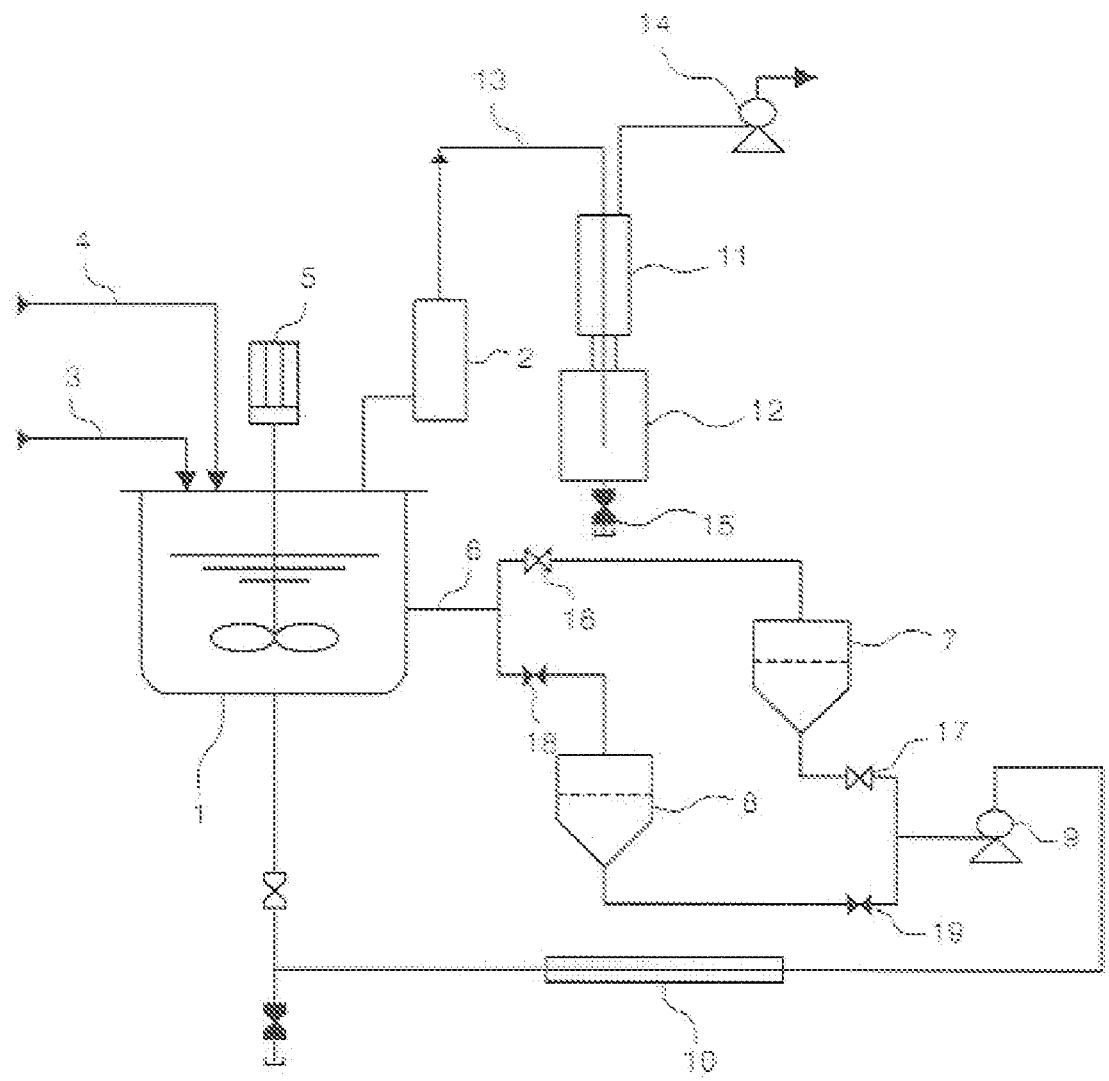
FIG. 1 is a schematic view showing a process of and a reaction system for the continuous production of octafluorocyclopentene, featuring the circulation of KF/DMF in accordance with an embodiment of the present invention.

Starting with $C_5Cl_8$, $C_5F_8$ gas 99.995 vol % pure with a content of 50 vol % or less of nitrogen gas, 5 vol % or less of oxygen gas, 5 vol ppm or less of water and 5 wt ppb or less of metal ingredients is produced in a continuous manner in accordance with a method of the present invention. The method of the present invention can be divided into two processes: continuous conversion of $C_5Cl_8$ into $C_5F_8$ with KF (first process); and purification of crude $C_5F_8$ to a highly pure form (second process).

These two processes are linked without interruption in the method of the present invention.

In the first process, KF.2HF may be used, instead of KF, to continuously convert $C_5Cl_8$ to $C_5F_8$.

First Process: Continuous Conversion of $C_5Cl_8$ to $C_5F_8$

With $C_5Cl_8$ used as a starting material, the production of crude $C_5F_8$ (first process) is achieved by fluorination not with hydrogen fluoride, but with potassium fluoride.

In the method of the present invention, the reaction solvent DMF is circulated at a rapid speed from a middle portion of the reactor to a lower portion with the aid of a pump. In a pipe through which DMF is circulated, two filter systems charged with potassium fluoride are installed in parallel. First, one of them is adapted to allow the rapidly circulating DMF to introduce potassium fluoride into the reactor. Then, the material $C_5Cl_8$ is fed into the reactor when the temperature reaches 140-150° C. As the fluorination proceeds in one of the two filter systems charged with potassium fluoride, KCl is generated. At the time of termination of the reaction, a valve is operated to turn the DMF stream toward the other fresh filter system so that DMF proceeds into the reactor without interruption, thereby continuously conducting the conversion of $C_5Cl_8$ into $C_5F_8$. The filter system in which KF vanished completely, that is, in which KCl was generated, is separated from the KCl by a simple operation, followed by feeding fresh KF into the filter system, which is then ready for the next round of fluorination. In this way, the conventional method in which feeding and converting the material is interrupted upon the replacement of KF with fresh KF can be overcome. That is, because it makes it possible to continuously feed $C_5Cl_8$ into the reactor and produce $C_5F_8$, the method of the present invention is very useful. As the reaction of potassium fluoride proceeds with $C_5Cl_8$, the amount of potassium chloride increases, resulting in a decrease in the reaction rate. Just before the completion of the reaction, the filter system in use is switched with the ready filter system by valve operation so as to improve the reactivity. In addition, $C_5F_8$ can be produced at high yield simply by stirring the reactants in the reactor.

In an upper portion of the reactor, the produced $C_5F_8$ is separated from the reactants. In this regard, a heat exchanger is installed in the upper portion to remove $C_5F_8$ from partially fluorinated products and the solvent DMF. When the heat exchanger is maintained at the boiling point of $C_5F_8$, 27° C., $C_5F_8$ can be discharged. However, since $C_5F_8$ stays for a long period of time in the reactor in the course of heat exchange in the heat exchanger, it is decomposed to a ring-broken compound under the high-temperature condition. Therefore, the produced $C_5F_8$ is rapidly discharged when the heat exchanger is operated at as low as 20-25° C. with a vacuum maintained at about 500-550 torr. The vacuum condition is controlled so as to set forth a temperature condition suitable for discharging the product. Compared to when a vacuum condition is not set forth, the production of by-products is significantly restrained when the heat exchanger is evacuated. After being discharged through the heat exchanger installed at an upper portion of the reactor, $C_5F_8$ is carried to a storage bath equipped with a heat exchanger having a coolant circulating at −30~−40° C. therein. In a vacuum condition of 500-550 torr, set forth in an upper portion of the heat exchanger, $C_5F_8$ is directed into the storage bath. The composition thus obtained through the reaction comprises $C_5F_8$ to a purity of 80 vol % or higher.

Second Process: Purification of $C_5F_8$ by Removal of Nitrogen, Oxygen and Low Boiling-Point Organics The product composition obtained in the first process contains oxygen and nitrogen in an amount ranging from hundreds vol. ppm to thousands vol. ppm whether the impurities are de novo present in the reactant materials or are incorporated upon a water-washing process or a drying process. In addition, C4 or C5 compounds, which are lower in boiling point than $C_5F_8$ and indefinite in structure, are also contained in an amount of hundreds vol. ppm in the product composition.

In accordance with the present invention, the impurites, such as nitrogen, oxygen, and the low boiling point organics, can be removed through a first distillation tower without the addition of an inert gas of Group 0, particularly helium gas. Provided for removing low-boiling point materials, first the distillation tower useful in the present invention consists of a heating bath, a distillation column, and a cooling condenser. The distillation column has 50 or more theoretical plates, and preferably 60 or more theoretical plates. Before the operation of the first distillation tower, a high vacuum of $10^{-4}$ torr or less is set forth inside the first distillation tower to remove residual low-boiling point components therefrom. Repeating vacuumization and devacuumization with $C_5F_8$ results in complete removal of the residual nitrogen and oxygen. The devacuumization is conducted by feeding a separate material, which comprises 50~85 vol % of $C_5F_8$ and is deprived of acid and moisture, into a middle portion of the first distillation tower for removing low boiling point components. When a heating bath is charged with the crude $C_5F_8$, it is subjected to total reflux. In this regard, a reflux ratio of 3~5 is suitable. Preferably, a temperature similar to the boiling point of $C_5F_8$ is set forth at a top portion of the first distillation tower. As for the pressure to be set forth in the first distillation tower, it depends on the concentration of the low boiling point materials and the discharged amount thereof, and preferably ranges from 0.3 to 0.5 gauge pressures in consideration of the transfer to the next tower (second tower for removing high boiling point 5 materials).

As total reflux is conducted, low boiling point materials are collected at the upper portion of the rectification tower while $C_5F_8$, free of low-boiling point materials, is directed, along with high boiling point materials, toward the bottom portion thereof. The low boiling point materials from the first distillation tower are analyzed at regular intervals with GC-DID (Gas Chromatography-Discharge Ionization Detector, Gow-Mac 590 series) used for nitrogen, oxygen and inert gas and GC-FID (Gas Chromatography-Flame Ionization Detector) used for other low boiling point organic compounds. During the production of highly pure etching gas for semiconductor processes, it must be analyzed on-line for low boiling point impurities (e.g., oxygen, nitrogen, inert gas). If a sample is taken or transferred for analysis, gas, such as oxygen and/or nitrogen, is highly apt to be incorporated thereinto, making accurate analysis practically impossible. In order to increase the accuracy of analysis, the instrument must be normalized using a standard curve plotted with three different standard concentrations (1 vol. ppm, 10 vol. ppm and 50 vol. ppm) just before each analysis. The standard slope of the curve is used to calculate the analyzed value.

When it is taken from a stream of the product in order to analyze the impurities, a sample is incorporated with nitrogen and oxygen from the air, so that accurate analysis is difficult to accomplish. In order to avoid this, the present invention adopts on-line analysis technique. In this an regard, an analysis line is connected to a low portion of the first distillation tower so as to directly introduce the $C_5F_8$, collected thereat, into the analyzer. If impurities, such as nitrogen, oxygen and organic compounds having a lower boiling point than octafluorocyclopentene, are detected at a level lower than a predetermined value upon the regular on-line analysis, the product composition is transferred to the second distillation tower for removing high boiling point materials. Meanwhile, the low boiling point materials collected in the top portion of the distillation tower having a fixed pressure maintained therein are discharged, together with a portion of $C_5F_8$. The discharged materials are directed toward an auxiliary distillation tower in which the $C_5F_8$ is separated from low boiling point materials. From the auxiliary distillation tower, $C_5F_8$, free of the low boiling point materials, is returned back to the storage bath of the first distillation tower.

Elution peaks obtained from the on-line analysis which is conducted in real time with the materials discharged from the lower portion of the first distillation tower show that elution peaks are detected at positions lower than 0.1 vol. ppm, the detection limit of GC-DID and GC-FID, showing that impurities, such as nitrogen, oxygen, inert gas, and organics, having boiling points lower than that of $C_5F_8$, can be completely removed only by heating reflux without incorporating the gas of Group 0.

Second Process: Purification of $C_5F_8$ by Removal of High Boiling-Point Organics and Water The octafluorocyclopentene efflux from the first distillation tower, which is free of low-boiling point organics, but contains high boiling point organics, is transferred to the second distillation tower for removing high boiling point organics. The pressure difference between the first and the second distillation towers is the force for transferring the efflux from the first to the second distillation tower. The amount of the efflux transferred is controlled using a flow meter. The theoretical plate of the second distillation tower more is than that of the first distillation tower, and amounts to 60 and preferably 70 or greater. The second distillation tower uses a structure packing (65 theoretical plates) made from teflon resin as a filler. Particularly, pipes, tubes, vessels, columns, and heat exchangers, all of which are electropolished, are installed inside the distillation tower in order to prevent metal ingredients from leaking out therefrom.

The amount of the metal ingredients leaking from electropolished equipment is tens ppb to hundreds ppb lower than that of the metal ingredients leaking from non-electropolished equipment. Like the first distillation tower, the second distillation tower is evacuated of impurities before the transfer of the materials. The cleansing work is conducted for a longer period of time for the second distillation tower than for the first distillation tower. After being purged, the second distillation tower is charged to a predetermined level with the high boiling point organic containing $C_5F_8$ efflux from the lower portion of the first distillation tower, and is fluxed by heating. Preferably, a temperature similar to the boiling point of $C_5F_8$ is set forth at a top portion of the second distillation tower. As for the pressure to be set forth in the second distillation tower, it preferably ranges from 0.1 to 0.2 gauge pressures. Depending on the capacity of the upper portion of the second distillation tower, the reflux ratio is preferably 5 or higher.

When a suitable reflux condition is met, the purified $C_5F_8$ is analyzed before being transferred. If it is analyzed to have a purity of 99.99 vol % (preferably 99.995 vol % or higher), the $C_5F_8$ is allowed to move through the upper portion of the second distillation tower to an electro-polished storage bath equipped with a heat exchanger.

The efflux of the highly pure $C_5F_8$ from the upper portion of the second distillation tower, that is, from the heat exchanger installed therein, functions to prevent the incorporation of residual metallic ingredients or water thereinto as much as possible, and particularly shows the effect of removing ones wt ppb more metallic ingredients, compared to that from the lower portion of the second distillation tower. This is because the $C_5F_8$ is eluted as a gas from the heat exchanger. The gaseous $C_5F_8$ is liquefied, condensed and stored in the storage bath equipped with a heat exchanger. After being taken and pre-treated, a predetermined volume of the $C_5F_8$ stored in the storage bath is analyzed on-line for metallic ingredients using ICP-MS (Perkin Elmer, DIC-II) and for water content using FT-IR (MIdac).

As the distillation proceeds, high boiling point materials accumulate in the lower portion of the second distillation tower, and are exemplified by 1-chloroheptafluorocyclopentene, 1,2-dichlorohexafluoropentene, and 1,2,3-trichloropentafluorocyclopentene. These high boiling point compounds are discharged from the second distillation tower with the solution level controlled therein, and then returned back to the reactor for production of the octafluorocyclopentene.

First Process: Production of Octafluorocyclopentene by Use of KF.2HF.

$C_5F_8$ be can be produced by reacting $C_5Cl_8$ with hydrogen fluoride at 120~140° C. in a solution of KF.2HF. To a reactor is added KF.HF and then about 38~40 wt % of hydrogen fluoride, followed by gradually raising the reaction temperature to yield KF.2HF. Afterwards, $C_5Cl_8$ and hydrogen fluoride are fed at a weight ratio of about 1:8 to 1:10 into the reactor. After fluorination, the resulting product solution comprising $C_5F_8$, hydrogen chloride, and a small amount of hydrogen fluoride is discharged from a heat exchanger installed in the upper portion of the reactor. The solution is passed through a reflux of water and an alkali solution to wash acid therefrom, and directed toward a drying process and then a distillation process. The final solution thus obtained comprises $C_5F_8$ at a purity of 50 vol %.

Highly useful for use in semiconductor processes, the gas produced, as described above, by conducting a first process for removing boiling low point materials with the aid of an auxiliary distillation tower and a second process for removing high boiling point materials in parallel contains $C_5F_8$ at a purity of 99.995 vol % or greater with a content of 5 wt ppb or less of metallic ingredients (aluminum, calcium, copper, iron, magnesium, manganese, nickel, zinc, etc.), 50 vol ppm or less of nitrogen gas, 10 vol ppm or less of oxygen, and 5 wt ppm or less of water.

A better understanding of the present invention may be realized with the following examples, which are set forth to illustrate, but are not to be construed to limit the present invention.

EXAMPLE 1

Conversion of $C_5Cl_8$ into $C_5F_8$

First Process

<Continuous Production of Crude $C_5F_8$ by Circulation of KF/DMF>

$C_5F_8$ was converted from $C_5Cl_8$ using the apparatus shown in FIG. 1.

Apparatus for the Production of $C_5F_8$
1. Reactor
2. Heat exchanger
3, 4. Pipes
5. Stirrer
6. Pipe
7. and 8. Filters
9. Pump
10. Double pipe
11. Heat exchanger
12. Primary storage bath
13. Pipe
14. Vacuum pump
15. Secondary storage bath pipe Process for Production of $C_5F_8$ 1) Each of the filters 7 and 8, having an internal capacity of 20 L, was charged with 14 kg of KF. Of the filters, one, for example, the filter 7 was allowed to communicate with the reactor 1 by opening the mid valve 16 and the lower valve 17.60 L of DMF was fed into the reactor 1 through the pipe 3 while a cooling medium maintained at a temperature 0~10° C. lower than the boiling point of $C_5F_8$ (for example, water 17~27° C.) was circulated in the heat exchanger 2 installed over the reactor 1. When the stirrer 5 was operated, steam was supplied to a jacket on the outer circumference of the reactor so as to heat the reactor to 135~140° C. At this time, the DMF-circulating pump 9 was allowed to run to bring DMF into contact with KF in the filter 7.

The reactor 1 is made from stainless steel and has an internal volume of 100 L and a steam jacket installed on the outer circumference thereof.

2) When the temperature of the reactor increased, the vacuum pump 14 installed over the primary storage bath 12 was operated to decrease the pressure of the storage bath to 500~550 torr. When the temperature of the reactor reached a predetermined value, $C_5Cl_8$ gas having a purity of 99% was provided at a rate of 1.57 mol/hour (540 g/hour) through the pipe 4 to the reactor 1. When production reaction of the product ($C_5F_8$) started, the heat exchanger was controlled to have a temperature similar to the boiling point of $C_5F_8$.

3) After reaction for about 12 hours, the valves 16 and 17 for the filter 7 in use were slowly closed while the valves 18 and 19 for the filter 8 were slowly opened, so that the exhausted filter could be replaced with a fresh one. Then, the exhausted filter 7 was dried to remove KF and KCl therefrom and charged again with 14 kg of fresh KF to prepare for another round of the fluorination.

4) The $C_5F_8$ thus obtained was produced at a rate of 0.292 kg/hour and had a purity of 83.5 wt %.

During the conversion of $C_5Cl_8$ to $C_5F_8$, organics produced through side-reactions, unreacted materials, metallic trace ingredients, and water remained as impurities.

Found in the product solution were about 0.12 vol % of two low boiling point materials whose structures were unknown, high boiling point materials including about 3.87 vol % of $C_5F_7Cl$, about 3.18 vol % of $C_5F_6Cl_2$, about 1.59 vol % of $C_5F_5Cl_3$ and about 5.42 vol % of ring-broken compounds in addition to 300 ppb of metal ingredients such as Ni, Fe, Mg, Al, etc., and the solvent (DMF).

The organics generated through side reactions can be divided into compounds having boiling points higher and lower than that (26.8° C.) of $C_5F_8$, which are called low boiling point materials and high boiling point materials, respectively.

After being stored in the primary storage bath 12, $C_5F_8$ was transferred through the pipe connected to a lower portion of the primary storage bath to the second storage bath (not shown) for preparation for the second process.

<Purification of Crude $C_5F_8$ (Second Process)>

Figure 2:
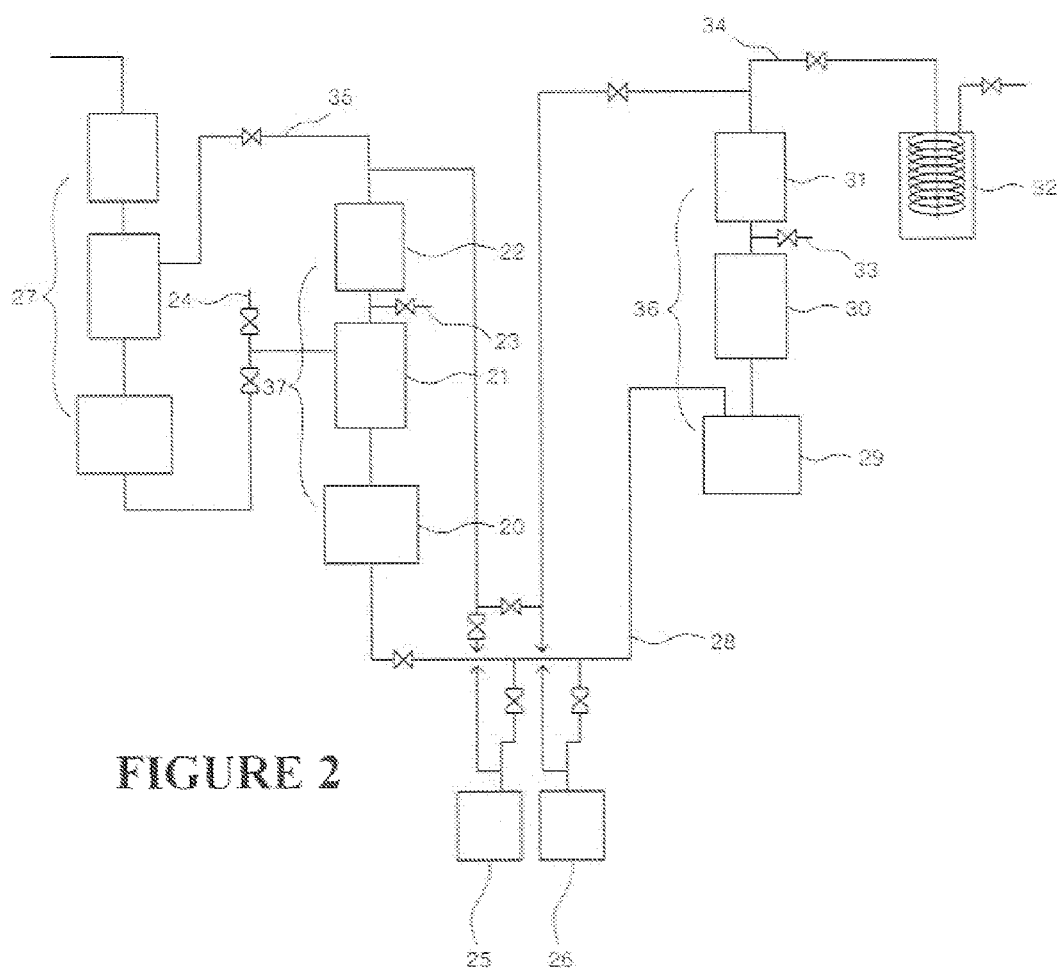
FIG. 2 is a schematic view showing a process of and a reaction system for purification of octafluorocyclopentene in the accordance with an embodiment of the present invention.

Removal of Low-Boiling Point Materials (FIG. 2)

1) A first distillation tower 37 for removing low boiling point materials, consisting of a 10 L heating reflux bath 20, a distillation column 21 equipped with a 3-inch structure packing (55 theoretical plates), and a heat exchanger 22, was evacuated to a pressure of $10^{-4}$ torr or higher so that the crude $C_5F_8$ was introduced several times thereto to completely remove nitrogen and oxygen therefrom.

2) While a coolant having a boiling point similar to that of $C_5F_8$ was passed through the heat exchanger in the vacuum condition, the crude $C_5F_8$ with a purity of 83.5 wt %, obtained in the first process, was fed at a rate of 200 g/hour through an inlet 24 positioned at an upper portion of the distillation column.

3) As the heat reflux bath 20 started to be charged with the crude $C_5F_8$, a heat carrier was circulated through the heat reflux bath 20 to reflux the crude $C_5F_8$. When the pressure of the distillation tower reached 0.5 gauge pressure, low-boiling point materials were discharged through the outlet 35 positioned at an upper portion of the first distillation tower to an auxiliary distillation tower 27.

4) A portion of the purified $C_5F_8$ was taken though a lower valve of the heat reflux bath 20 to analyzers 25, 26 in which on-line analysis was conducted in real time. As the distillation proceeded, peaks for nitrogen, oxygen and low boiling point materials disappeared from the analysis graph (analysis limit 0.1 vol ppm), remaining as traces. As analyzers useful in the present invention, GC-DID (Gas Chromatography-Discharge Ionization Detector, Gow-Mac) was used for analyzing nitrogen, oxygen and inert gas, and GC-FID (Gas Chromatography-Flame Ionization Detector) was used for analyzing organics.

5) The discharge from the upper outlet 35 of the distillation tower was determined to contain 450 vol ppm of nitrogen and 25 vol ppm of oxygen, using the analyzer 25, and two structure-indefinite, low-boiling point organic compounds in amounts of 735 vol ppm and 455 vol ppm, respectively, using the analyzer 26.

6) When the discharge from the lower portion of the heat reflux bath was analyzed to have low-boiling point materials at a trace level, beyond the analysis limit of the analyzer, upon the on-line analysis, it was transferred to a second distillation tower 29 for removing high-boiling point materials. At this time, the $C_5F_8$ had a purity of 71.5~75.4 vol %.

7) The effluent, containing high concentrations of nitrogen, oxygen and low-boiling point materials from the upper outlet 35 of the first distillation tower, was carried to the auxiliary distillation tower 27, having the same structure as the first distillation tower, in which $C_5F_8$ was again separated from effluent then back to the first the and returned distillation tower 37.

8) From the lower portion of the first distillation tower, $C_5F_8$ was discharged at a rate of 35~45 g/hour through the carrier pipe 28 to the second distillation tower. The low-boiling point materials were removed in the distillation column of the first distillation tower 21.

Removal of High-Boiling Point Materials, Water and Metal Ingredients

1) A second electro-polished distillation tower, consisting of a 10 L heat reflux bath 29, a distillation column 30 equipped with a 3-inch structure packing (Teflon resin, 65 theoretical plates), and a heat exchanger 31, was evacuated to a pressure of $10^{-4}$ torr or greater and the $C_5F_8$, free of low-boiling point materials, was carried from the bottom of the heat reflux bath 20 through a pipe 28.

2) In the vacuum condition, a coolant maintained at a temperature (preferably 15~20° C.) lower than the boiling point of $C_5F_8$ was passed through the heat exchanger 31 while the $C_5F_8$, free of low-boiling point materials, was carried at a rate of 155~165 g/hour from the heat reflux bath 20 through the pipe 28 to the heat reflux bath 29 of the second distillation tower for removing high-boiling point materials.

3) As the heat reflux bath 29 started to be charged with the low-boiling point material-free $C_5F_8$, a heat carrier was circulated through the heat reflux bath 29 to reflux the $C_5F_8$. In this regard, a greater amount of the heat carrier was used in the heat reflux bath 29 than in the reflux bath 20 of the first distillation tower in order to further increase the reflux ratio. When the pressure of the distillation tower reached 0.5 gauge pressures as a result of the circulation of the coolant, the distilled $C_5F_8$ was discharged as a highly pure gas from an 34 top positioned at the of the second outlet distillation tower and directed toward electro-polished storage 32 equipped with a heat exchanger.

Owing to their weight, metal ingredients could not be contained in the gaseous $C_5F_8$.

The distilled $C_5F_8$ was produced at a rate of 110~120 g/hour and analyzed to have a purity of 99.997 vol %, 13 vol ppm of nitrogen, and 3 vol ppm of oxygen, and water and metal ingredients were contained in amounts as shown in Table 1, below.

4) In Table 1, the distilled $C_5F_8$ discharged from the upper outlet 34 of the second distillation tower was compared to that discharged from the lower outlet 33 with respect to contents of metal ingredients and water. Particularly, a large difference in the content of each metal ingredient was found between the discharges from the first distillation tower and the electro-polished distillation tower. Therefore, the distillated $C_5F_8$ discharged from the upper outlet 34 of the electro-polished second distillation tower is useful as a gas for semiconductor processes, which requires 5 wt ppb or less of metal ingredients.

TABLE 1

| Samples taken from | Metals (wt ppb) | | | | | | | | | Water (wt ppm) |
|---|---|---|---|---|---|---|---|---|---|---|
| | Al | Ca | Cu | Fe | Mg | Mn | Ni | Na | Zn | |
| 1st Distillation Tower (bottom of heat exchanger) | 16 | 13 | 8 | 22 | 10 | 11 | 19 | 7 | 6 | 6 |
| 2nd Distillation Tower (bottom of heat exchanger) | 6 | 6 | 4 | 13 | 3 | 3 | 10 | 3 | 2 | 3 |
| 2nd Distillation Tower (top of heat exchanger) | <1 | <1 | 1 | 2.2 | <1 | <1 | 1.5 | 2.2 | <1 | 1 |

EXAMPLE 2

The production of $C_5F_8$ (first process) was achieved in the following manner.

<Production of Low Purity of Crude $C_5F_8$ by Use of KF.2HF (First Process)>

Figure 3:
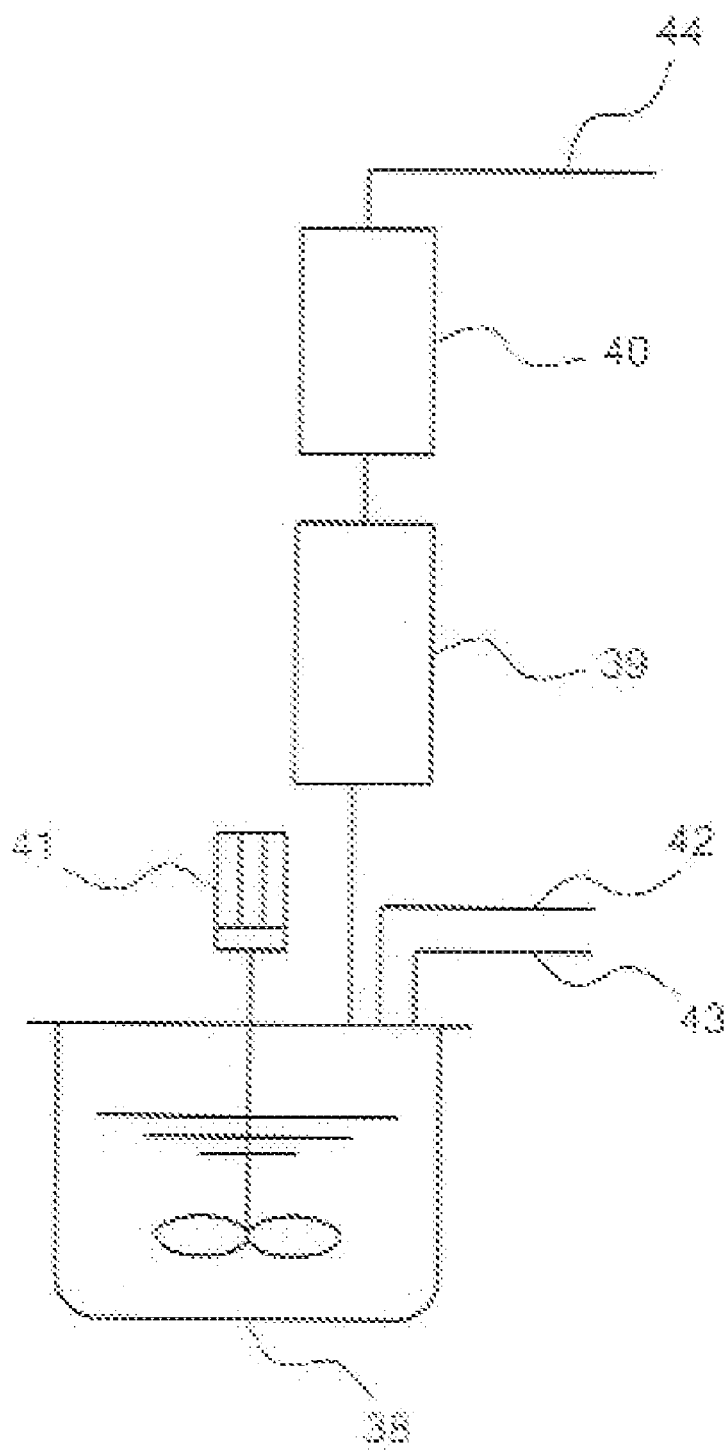
FIG. 3 is a schematic view showing a process of and a reaction system for the production of octafluorocyclopentene, featuring the use of KF.2HF.

$C_5F_8$ was produced using the reaction system shown in FIG. 3.

Reactor

38. Reaction bath
39. Distillation column
40. Heat exchanger
41. Stirrer
42. Inlet for $C_5Cl_8$
43. Inlet for HF
44. Outlet for product Production Technique 1) To a 5 L stainless steel compulsory reactor 38 was fed 4.3 kg of KF.HF which was then heated to 80° C. 1.3 kg of hydrogen fluoride was slowly added to the reactor to solidify the content, followed by raising the temperature to 120° C.

2) The temperature of the heat exchanger 40 was set at about 20° C. and when the temperature of the reactor reached a predetermined value, $C_5Cl_8$ and HF were fed at rates of 60.0 g/hour and 34.9 g/hour to the reaction bath through the inlets 42 and 43, respectively.

3) The $C_5F_8$ effluent was washed with alkali and dried. It was produced at a rate of 20.73 g/hour and had a purity of 52.5%.

As described hereinbefore, highly pure $C_5F_8$, useful as dry etching gas for use in VISI or ULSI processes, can be produced from $C_5Cl_8$ in a continuous manner in accordance with the present invention.

Although the preferred embodiments present of the invention have been disclosed for illustrative purposes, those skilled in the art will appreciate that various modifications, additions and substitutions are possible. Accordingly, the modifications, additions and substitutions should be understood as falling within the scope and spirit of the invention.

We claim:

1. A method for preparing dry-etching gas comprising:
    heating to reflux octachlorocyclopentene with a reaction solvent by selecting one of a pair of KF-charged filters arranged in parallel so as to form crude octafluorocyclopentene;
    removing materials having low boiling points by heating to reflux the crude octafluorocyclopentene in a low boiling distillation tower through fraction distillation; and
    removing metal ingredients and materials having a boiling point higher than a boiling point of the octafluorocyclopentene by heating to reflux the resulting octafluorocyclopentene in a high boiling distillation tower through fraction distillation, the step of removing metal ingredients occurring after the step of removing materials having a low boiling points.

2. The method of claim 1, the other of the KF-charged filters being subjected to fraction distillation continuously by heating to reflux in the low boiling distillation tower and the high boiling distillation tower.

3. The method of claim 1, said reaction solvent being N,N-dimethylformamide.

4. The method of claim 1, said resulting octafluorocyclopentene comprising octafluorocyclopentene in an amount of no less than 99.995 volume percent and nitrogen gas in an amount of no more than 50 ppm of volume and oxygen in an amount of no more than 5 ppm of volume and water in an amount of no more than 5 ppm of weight and metal ingredients in an amount of no more than 5 ppb by weight.

5. A method of preparing a dry-etching gas comprising:
    reacting octachlorocyclopentene with KF-2HF in a reactor in order to form crude octafluorocyclopentene;
    removing materials having low boiling points by heating to reflux the crude octafluorocyclopentene in a low boiling distillation tower through fraction distillation; and
    removing metal ingredients and materials having a boiling point higher than a boiling point of the octafluorocyclopentene by heating to reflux the resulting octafluorocyclopentene in a high boiling distillation tower through fraction distillation, the step of removing metal ingredients occurring after the step of removing materials.

6. The method of claim 5 the step of reacting octachlorocyclopentene with KF-2HF occurring at a temperature of between 120° C. and 140° C.

* * * * *